US00PP09598P

United States Patent [19]

Skotak, Jr.

[11] Patent Number: Plant 9,598

[45] Date of Patent: Jul. 2, 1996

[54] NEOREGELIA PLANT NAMED 'SHEBA'

[75] Inventor: Chester Skotak, Jr., Alajuela, Costa Rica

[73] Assignee: Dura Flor S.A., Alajuela, Costa Rica

[21] Appl. No.: 422,532

[22] Filed: Apr. 14, 1995

[51] Int. Cl.[6] ..... A01H 5/00

[52] U.S. Cl. ..... Plt./88.8

[58] Field of Search ..... Plt./88.8

*Primary Examiner*—James R. Feyrer

*Attorney, Agent, or Firm*—Foley & Lardner

[57] ABSTRACT

A new and distinct Neoregelia named 'Sheba,' characterized by its finely serrated leaf margins; white (RHS 158A-B) leaf margins; dark green (RHS 141A-B) leaf centers; basal portion of the innermost leaves that is red (RHS 57A-B) with white and green spots and a distal margin that is dark red (RHS 59A-B); and a low and spreading rosette plant habit.

3 Drawing Sheets

The present invention comprises a new and distinctive cultivar of Neoregelia hybrid, hereinafter referred to by the cultivar name 'Sheba.' Neoregelia species are tank epiphytes with stemless inflorescences and flowers that barely rise above the water in the centers of plants. 'Sheba' can be advantageously grown as a single pot plant in order to display its symmetrical rosette plant habit and colorful foliage.

The new cultivar is a product of a planned breeding program, and was originated from a cross made during such a program in Balsa, Costa Rica in 1990. The female, or seed parent was *Neoregelia carolinae*×*Neoregelia McWilliamsii.* The male, or pollen parent was *Neoregelia McWilliamsii.*

'Sheba' was discovered and selected as a flowering plant within the progeny of the stated cross by Chester Skotak, Jr. in 1992 in a controlled environment in Balsa, Costa Rica. Subsequent asexual reproduction by removal of offsets has demonstrated that the combination of characteristics as herein disclosed for the new cultivar are firmly fixed and are retained through successive generations of asexual reproduction.

The new cultivar has not been observed under all possible environmental conditions. The phenotype may vary with variations in environment such as temperature, light intensity and day length, without any variation in the genotype of the plant.

The following traits have been repeatedly observed and are determined to be basic characteristics of this Neoregelia and in combination distinguish 'Sheba' as a new and distinct cultivar:

1. 'Sheba' has finely a serrated leaf margin.
2. The leaf margin is white (RHS 158A-B) with a width of approximately 3 to 8 mm at the widest point of the leaf.
3. The center portion of the leaf is dark green (RHS 141A-B).
4. The basal portion of the innermost leaves is red (RHS 57A-B) with white and green spots and distal margin that is RHS 59A-B.
5. The plant habit is a low and spreading rosette.

The following observations, measurements and values describe plants grown in Balsa, Costa Rica and Goulds, Fla., U.S.A. under greenhouse conditions which closely approximate those generally used in horticultural practice. Color references are made to the Royal Horticultural Society (RHS) Colour Chart, except where general color terms of ordinary significance are used. The color values were determined at approximately 3:00 p.m. on Apr. 11, 1995 under natural light in Washington, D.C., U.S.A.

The new cultivar can be compared to *Neoregelia McWilliamsii.* 'Sheba' has finely serrated leaf margins that are not present on *N. McWilliamsii.* In addition, *N. McWilliamsii* has variegated leaves while 'Sheba' has uniformly green leaves with white margins.

The accompanying photographic drawings show typical characteristics of the new cultivar, with colors being as true as possible with illustrations of this type.

Sheet 1 is a side view of the plant.

Sheet 2 is a top view of the plant.

Sheet 3 is a closeup of the center of the plant showing flowers.

Classification:

*Botanical.*—Neoregelia hybrid, cv. 'Sheba'.

*Commercial.*—Neoregelia 'Sheba'.

Parentage:

*Male parent.*—*Neoregelia McWilliamsii.*

*Female parent.*—*Neoregelia carolinae*×*Neoregelia McWilliamsii.*

Propagation: Vegetatively through removal of offsets.

Plant description: From 32 cm. to 40 cm. tall when grown in 12.5 cm. pots, and approximately 55–60 cm. in diameter when fully grown.

*Growth habit.*—Low spreading rosette.

Leaves:

*Form.*—Blades lingulate, broadly rounded and apiculate.

*Size.*—Length: 32 cm to 40 cm. Width: 2 cm tip–3 cm middle.

*Texture.*—Smooth upper and lower surface with finely serrated leaf margins.

*Veins or ribs.*—None.

*Color (RHS).*—Upper surface: The leaf margin is white (RHS 158A-B) with a width of approximately 3 to 8 mm. at the widest point of the leaf. The leaf color is dark green (RHS 141A-B). The basal portion of the innermost leaves is red (RHS 57A-B) with white and green spots and a distal margin that is RHS 59A-B. Lower surface: Same as upper surface.

*Number of leaves.*—Average 26 to 30.

Flowers:

*Arrangement.*—Inflorescence deeply sunken rosette — simple and many-flowered.

*Color.*—Dark blue.

*Fruit.*—Ovary ellipsoid and approximately 10 mm long and white to pink in color.

*Duration of flowers.*—Individually only 1 day — as a whole 1 month.

*Other significant characteristics.*—Center of rosette maintains red color up to 3 months.

Reproductive organs:

*Stamens.*—Pale yellow. Anther: White.

*Pistils.*—Ovary: Ellipsoid — approximately 10 mm long and 5 mm in diameter.

Resistance to disease: Resistant to Fusarium sp. and several other fungi found in in Costa Rica.

General observations: 'Sheba' grows vigorously and its appeal is enhanced by a uniformly low and spreading rosette habit with red center.

I claim:

1. A new and distinct cultivar of Neoregelia plant named 'Sheba,' as illustrated and described.

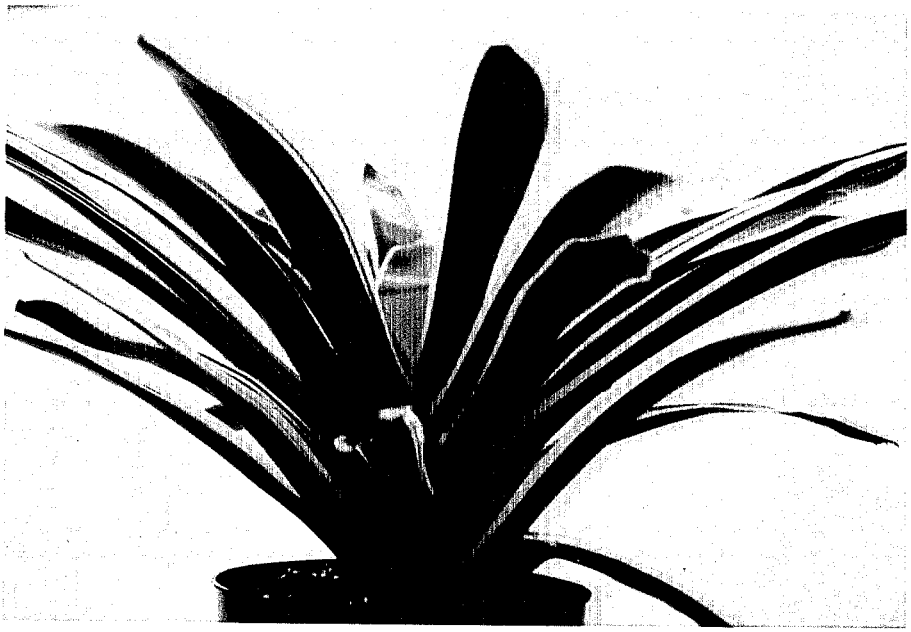

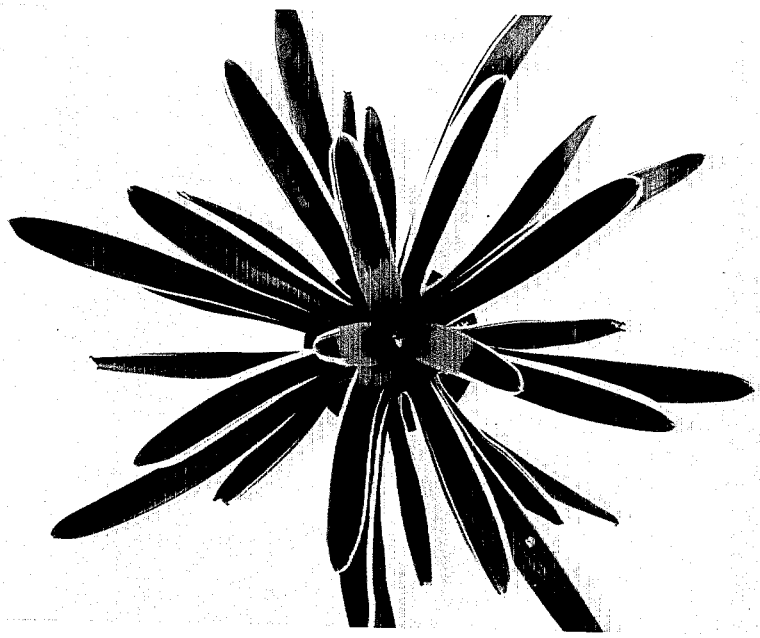

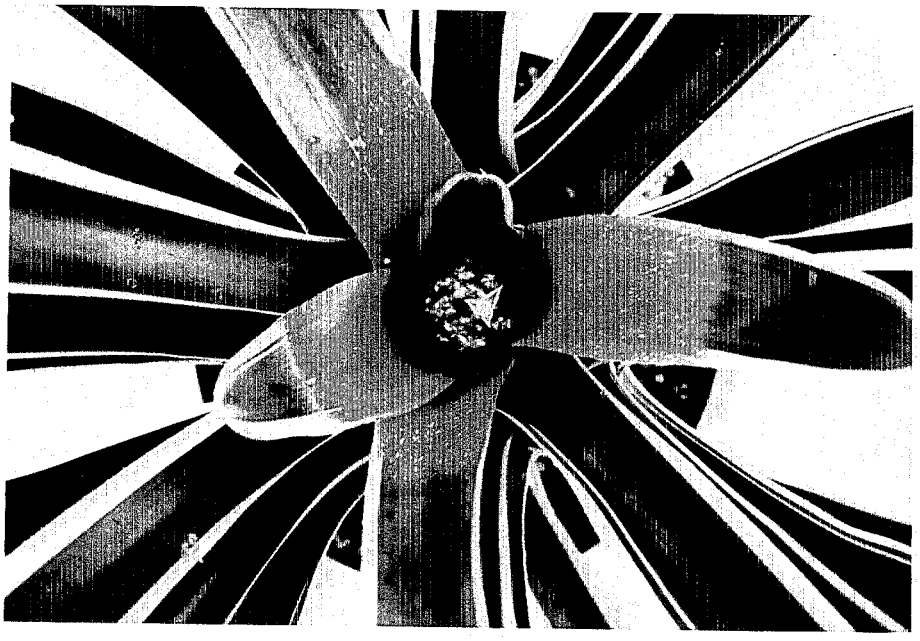

* * * * *